US010850025B2

(12) United States Patent
Bulloch et al.

(10) Patent No.: US 10,850,025 B2
(45) Date of Patent: Dec. 1, 2020

(54) ARRAYED MULTI-IV SET MANAGEMENT DEVICE

(71) Applicant: Somnus Medical, LLC, Roosevelt, UT (US)

(72) Inventors: Edwin T. Bulloch, Vernal, UT (US); Lucas Reichert, Roosevelt, UT (US)

(73) Assignee: Somnus Medical, LLC, Roosevelt, UT (US)

( * ) Notice: Subject to any disclaimer, the term of this patent is extended or adjusted under 35 U.S.C. 154(b) by 0 days.

(21) Appl. No.: 16/153,453

(22) Filed: Oct. 5, 2018

(65) Prior Publication Data

US 2020/0108200 A1 Apr. 9, 2020

(51) Int. Cl.
*A61M 5/14* (2006.01)

(52) U.S. Cl.
CPC .................... *A61M 5/1418* (2013.01)

(58) Field of Classification Search
CPC combination set(s) only.
See application file for complete search history.

(56) References Cited

U.S. PATENT DOCUMENTS

| | | | | |
|---|---|---|---|---|
| 2,888,546 A * | 5/1959 | Kinney | .................... | H05B 3/80 174/146 |
| 2,902,821 A * | 9/1959 | Kelly, Jr. | ............... | A44C 5/102 174/146 |
| 2,983,014 A * | 5/1961 | Greenwood | ............ | D06F 55/00 174/146 |
| 3,696,920 A * | 10/1972 | Lahay | .................... | A61B 50/20 206/370 |
| 4,654,026 A * | 3/1987 | Underwood | ........ | A61M 5/1418 128/DIG. 26 |
| D298,355 S * | 11/1988 | Young | .......................... | D24/128 |
| 5,027,478 A * | 7/1991 | Suhr | ..................... | B65H 75/36 137/355.16 |
| 5,316,246 A * | 5/1994 | Scott | .................. | A61M 5/1418 248/68.1 |
| 6,012,940 A * | 1/2000 | Wheeler | ............ | H01R 13/6392 439/369 |
| 6,360,051 B1 * | 3/2002 | Daoud | ................. | G02B 6/3801 385/134 |
| 6,552,270 B1 * | 4/2003 | Heacox | ................... | F16L 3/233 174/135 |
| 6,930,244 B1 * | 8/2005 | Nebel | ................. | B60R 16/0207 174/486 |

(Continued)

*Primary Examiner* — Monica E Millner

(57) ABSTRACT

A multi-IV set retention device for retaining flexible lines (e.g., medical fluid lines, such as IV sets) comprises a retention body having a normal axis, and a plurality of retention slots that removably receive and retain flexible lines, and a plurality of openings to facilitate insertion of a flexible line into an associated retention slot. The retention slots are radially arrayed about the normal axis of the retention body, such that the plurality of flexible lines is movable as a unitary body. The flexible lines can be radially bundled as a collection of flexible lines that define a center of mass about a central portion of the retention device, so that the flexible lines move and act as a single flexible line. One or more of such multi-IV set retention devices can be coupled along a length of one or more flexible lines, thus fanning an IV set retention system. A method of making the multi-IV set retention device, and a method of retaining flexible lines, is provided.

26 Claims, 7 Drawing Sheets

(56) References Cited

U.S. PATENT DOCUMENTS

| | | | | |
|---|---|---|---|---|
| 7,500,644 B2* | 3/2009 | Naudet | .................... | F02C 7/222 |
| | | | | 174/146 |
| 8,020,259 B2* | 9/2011 | Ho | .......................... | F16L 3/222 |
| | | | | 24/129 R |
| 9,520,705 B2* | 12/2016 | Trifeletti | ................. | H02G 13/40 |
| 9,692,220 B2* | 6/2017 | Schrader | .................... | F16L 3/12 |
| 9,837,802 B1* | 12/2017 | Welch | ...................... | H02G 1/08 |
| 9,856,998 B2* | 1/2018 | Cripps, II | ............... | F16L 3/222 |
| 9,951,888 B2* | 4/2018 | Boriack | ................... | F16L 3/223 |
| 2003/0173470 A1* | 9/2003 | Geiger | .................... | F16L 3/223 |
| | | | | 248/55 |
| 2007/0120023 A1* | 5/2007 | Martinez | ............... | E02F 9/2275 |
| | | | | 248/75 |
| 2007/0246613 A1* | 10/2007 | Kennedy | .................. | H02G 3/32 |
| | | | | 248/56 |
| 2009/0065249 A1* | 3/2009 | Silvers | ..................... | H02G 3/30 |
| | | | | 174/72 A |
| 2009/0272576 A1* | 11/2009 | Medina | ............... | B60R 16/0215 |
| | | | | 174/72 A |
| 2010/0132979 A1* | 6/2010 | Chen | ........................ | F16L 3/223 |
| | | | | 174/135 |
| 2011/0042529 A1* | 2/2011 | Walter | .................... | F16L 3/223 |
| | | | | 248/68.1 |
| 2011/0147542 A1* | 6/2011 | Hoek | ...................... | F16L 3/223 |
| | | | | 248/68.1 |
| 2015/0330552 A1* | 11/2015 | Boyanich | ................ | F16L 3/133 |
| | | | | 248/62 |

* cited by examiner

US 10,850,025 B2

ARRAYED MULTI-IV SET MANAGEMENT DEVICE

BACKGROUND

One of the major benchmarks of medical care was the introduction of an Intravenous (IV) set to access the circulatory system of a patient, enabling the administration of fluids and medications in a controlled, predictable manner. The typical IV set includes a primary fluid flow line of tubular construction with one or more access points. A number of such IV sets may be used in combination for delivering medical fluid to a patient. As such, a plurality of fluid flow lines may extend from fluid bag(s) and other medical devices to the patient. With a number of fluid lines traversing in a variety of different directions to the patient, the fluid flow lines are subject to tangling with each other and with other apparatuses, and even subject to being snagged or pulled accidentally by personnel or other apparatuses when being moved around a hospital room when attached to the patient.

To remedy this issue, existing fluid flow line clips or retention devices are typically coupled to the fluid lines to "collect" the IV sets in a group. However, these are commonly configured to arrange the IV sets about a plane, or in a linear or planar manner. This arrangement becomes unwieldy to move around because the fluid lines are arranged linearly or planar (i.e., within the same plane) relative to each other, which effectively results in a planar, unbalanced set or sheet of fluid flow lines that readily flop around and twist, which can pose problems to practitioners working around and moving the IV sets. This is because, when moving around a collection of fluid lines arranged in a plane in a variety of directions, the center of mass of the lines is constantly changing and constantly unbalanced. Moreover, the collection of IV sets tends to flex or bend easily along or about an axis parallel to the plane, but with difficulty about an axis normal to the plane, which makes the collection of IV sets difficult to move around and manage during medical care. When every second is valuable during many medical procedures, any delay or distraction unnecessarily caused by IV sets being collected and moved in this unwieldy manner can be problematic to the medical procedure at hand, and therefore to the patient.

BRIEF DESCRIPTION OF THE DRAWINGS

Features and advantages of the invention will be apparent from the detailed description which follows, taken in conjunction with the accompanying drawings, which together illustrate, by way of example, features of the invention; and wherein.

DETAILED DESCRIPTION

Figure 1A:
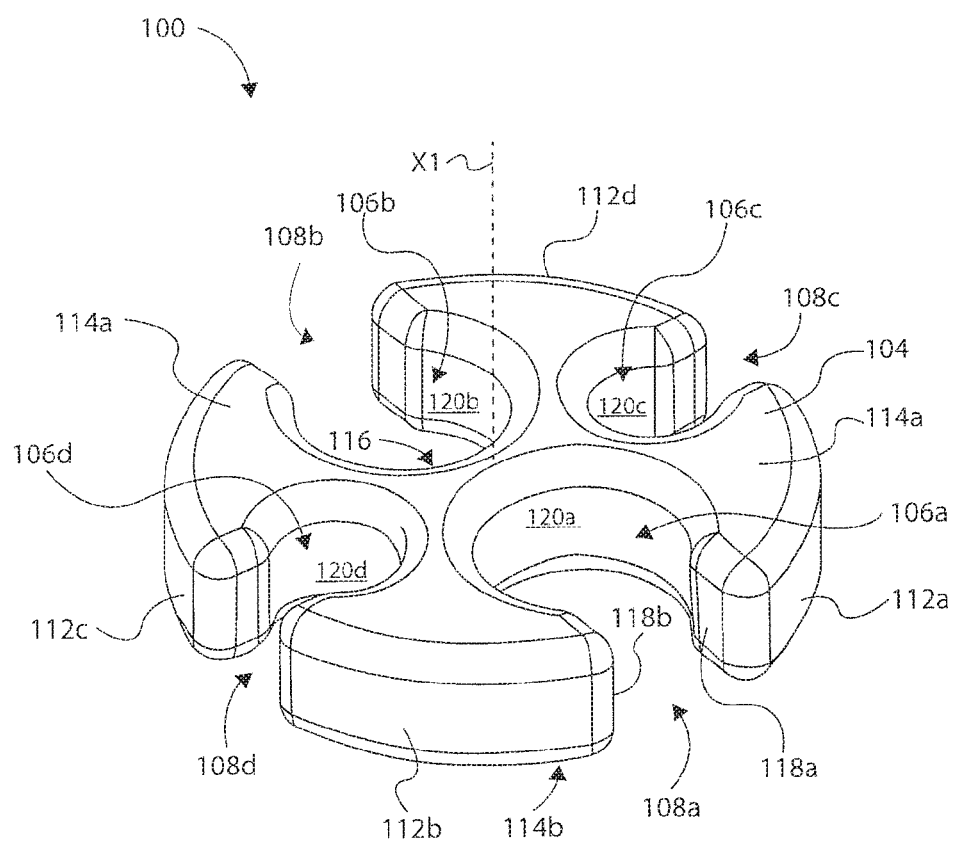
FIG. 1A illustrates an isometric view of a multi-IV set retention device for retaining and managing flexible lines of a plurality of IV sets, in accordance with one exemplary embodiment of the present invention.

As used herein, the term "substantially" refers to the complete or nearly complete extent or degree of an action, characteristic, property, state, structure, item, or result. For example, an object that is "substantially" enclosed would mean that the object is either completely enclosed or nearly completely enclosed. The exact allowable degree of deviation from absolute completeness may in some cases depend on the specific context. However, generally speaking, the nearness of completion will be so as to have the same overall result as if absolute and total completion were obtained. The use of "substantially" is equally applicable when used in a negative connotation to refer to the complete or near complete lack of an action, characteristic, property, state, structure, item, or result.

As used herein, "adjacent" refers to the proximity of two structures or elements. Particularly, elements that are identified as being "adjacent" may be either abutting or connected. Such elements may also be near or close to each other without necessarily contacting each other. The exact degree of proximity may in some cases depend on the specific context.

An initial overview of technology embodiments is provided below and then specific technology embodiments are described in summary and in further detail later. This initial summary is intended to aid readers in understanding the technology more quickly, but is not intended to identify key features or essential features of the technology, nor is it intended to limit the scope of the subject matter.

At the outset, an IV set is intended to mean a single IV line having a flexible line. An IV set system is intended to mean at least a plurality of IV sets within the IV set system. The IV set system can comprise additional elements operable within the IV set, such as a merging fluid pathway, a manifold, various access points, etc. An access point is intended to mean any point along the IV set in which access is provided to the fluid flow within the IV set. An access point can include such elements as access ports, spike/drip chambers, patient interconnect structures, fluid interconnect means, etc. An access port is intended to mean a specific type of access point that facilitates access to the fluid flow within the IV set, such as by push (e.g., using a syringe) or by infusion (e.g., through fluid coupling of another IV set).

The present disclosure sets forth a multi-IV set retention device for retaining and managing flexible lines of a plurality of IV sets comprising, a retention body having a normal axis; a plurality of retention slots formed through the retention body (each retention slot is sized to removably receive and retain a flexible line, such as that of an IV set); and a plurality of openings extending from a perimeter area of the retention body. Each opening is in communication with one of the plurality of retention slots, and each opening is operable to facilitate insertion of a. flexible line into an associated one of the plurality of retention slots for retention of the flexible line. The plurality of retention slots can be radially arrayed about the normal axis of the retention body.

In one example, the retention body comprises at least one outer curved surface at least partially defining the perimeter area.

In one example, each opening faces outwardly from a central portion of the retention body. The openings can outwardly face different directions relative to each other.

In one example, the plurality of retention slots are formed or arrayed in a non-linear manner about a curved plane parallel to the normal axis.

in one example, at least some of the retention slots are arrayed in an arc about the retention body.

In one example, adjacent retention slots are formed and oriented about respective planes oriented transverse to each other, which planes are parallel to and extend from the normal axis.

In one example, the normal axis is centrally located about the retention body relative to a central axis of each of at least two of the retention slots.

In one example, the perimeter area defined by the retention body is substantially circular shaped.

In one example, a first retention slot can comprise a first central axis situated generally along an x-axis of the retention body, and a second retention slot can comprise a second central axis situated generally along a y-axis of the retention body (from the perspective of viewing the retention body along the normal axis, which is also the z axis).

In one example, a first pair of retention slots can be situated generally along an x-axis of the retention body, and a second pair of retention slots can be situated generally along a y-axis of the retention body (again, from the perspective of viewing the retention body along the normal axis, which is also the z axis).

In one example, each retention slot comprises a radial line support surface substantially parallel to the normal axis and formed radially in at least 180 degrees.

In one example, each opening is sized less than an outer diameter of a flexible line received through the opening, such that the opening assists to retain the flexible line in the retention slot, and in sonic cases slidably retain the flexible line (i.e., the flexible line can slide within the retention slot relative to the multi-IV set retention device, such as is advantageous when bending or otherwise moving the collection of IV sets within the established or formed IV set retention system, wherein the various individual flexible lines can slide relative to the retention device to permit the collection of flexible lines to more easily bend as their bending is not interfered with by the retention device(s) retaining them).

In one example, a central axis of any one retention slot is substantially an equidistance from a central axis of any other retaining slot.

In one example, the retention body is substantially symmetrical along an x-axis and along a y-axis, such that, when a flexible line is retained in each of the retention slots, the multi-IV set retention device and the flexible lines move together essentially as unitary body having a longitudinal center of mass extending generally through a central portion of the retention body.

In one example, each retention slot comprises a central axis being substantially parallel to the normal axis, and the normal axis is centrally located relative to the central axes of at least two retention slots.

The present disclosure sets forth an IV set retention system for retaining a plurality of flexible lines, such as those of a plurality of IV sets (the plurality of IV sets being part of an IV set system, for example, when one or more IV sets are connected together, although this is not necessary), the IV set retention system comprising a plurality of flexible lines of a plurality of respective IV sets, and a plurality of multi-IV set retention devices removably coupled to the plurality of flexible lines. Each multi-IV set retention device comprises a retention body and a plurality of retention slots formed through the retention body, and each retention slot has an opening sized to removably receive one flexible line of the plurality of flexible lines. Each retention slot is sized to receive and retain the respective flexible line, and the plurality of retention slots are radially arrayed about the retention body. The multi-IV set retention devices are spaced apart from each other along a length of the plurality of flexible lines, such that the plurality of flexible lines is movable as a unitary body.

In one example, each flexible line comprises a longitudinal central axis that remains substantially parallel to the longitudinal central axes of other flexible lines when the flexible lines are moved along with the plurality of multi-IV set retention devices.

In one example, the unitary body defined by the plurality of flexible lines defines a central axis of the formed IV set retention device that extends through a central portion of each retention body.

In one example, the retention bodies are spaced apart at a minimum distance from each other, such that the flexible lines are bundled in a radial array, and such that each line is limited from substantial movement away from adjacent flexible lines.

In one example, the plurality of flexible lines comprises a plurality of fluid lines transferring a medical fluid through the fluid lines to a patient. The plurality of flexible lines, having the medical fluid therein, define a center of mass defined about a central portion of each retention body of respective multi-IV set retention devices, such that the plurality of fluid lines move and act as a single flexible line having a generally radial perimeter or perimeter profile defined by outward facing portions of the perimeters of the fluid lines.

The present disclosure sets forth a method of manufacturing a multi-IV set retention device for retaining flexible lines comprising forming a retention body; forming a plurality of retention slots through the retention body and forming a plurality of openings that extend from a perimeter of the retention body. Each opening is formed in communication with one of the plurality of retention slots, and each opening is operable to facilitate insertion of a flexible line, such as that of an IV set, into an associated one of the plurality of retention slots for retention of the flexible line. Forming the retention slots and openings comprises forming the plurality of retention slots to be radially arrayed about the retention body.

The present disclosure sets forth a method for retaining flexible lines with at least one multi-IV set retention device comprising providing a multi-IV set retention device comprising a retention body and a plurality of retention slots formed through the retention body, and each retention slot has an opening. The method includes coupling a flexible line of a plurality of flexible lines into each retention slot through the respective openings. The plurality of retention slots are radially arrayed about the retention body such that the plurality of flexible lines is movable as a unitary body.

Figure 1B:
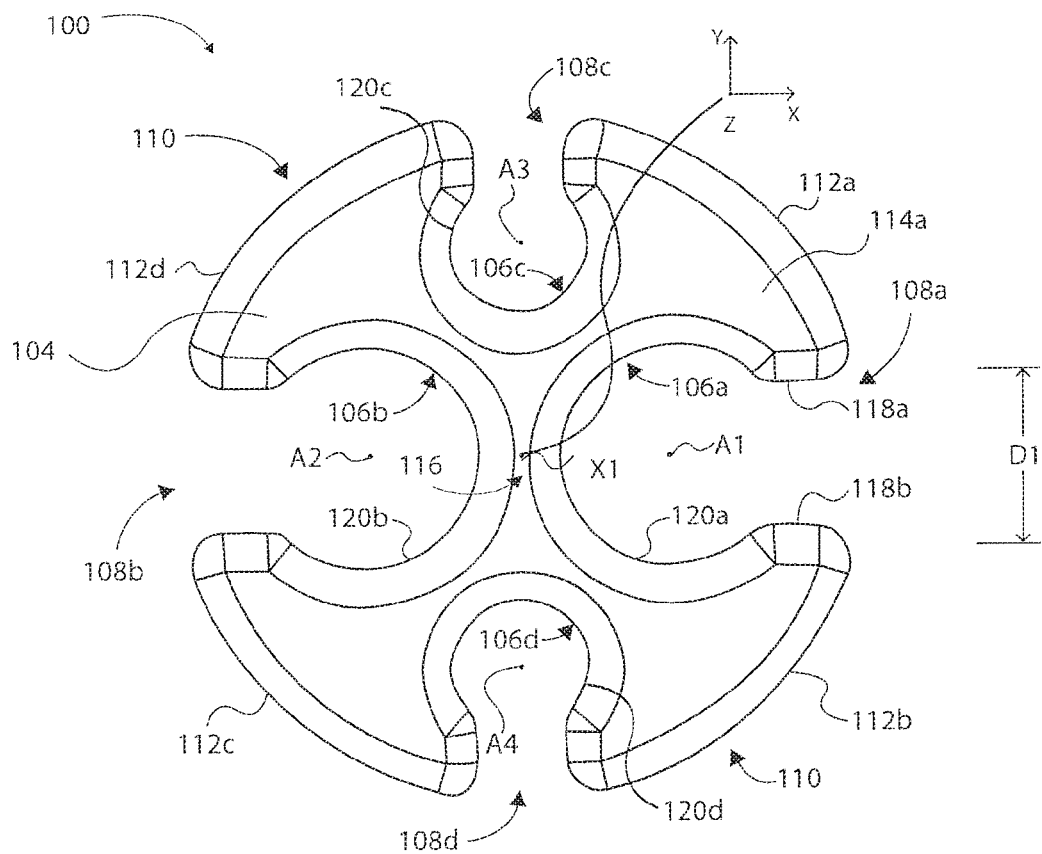
FIG. 1B illustrates a top view of the multi-IV set retention device of FIG. 1A.
Figure 1C:
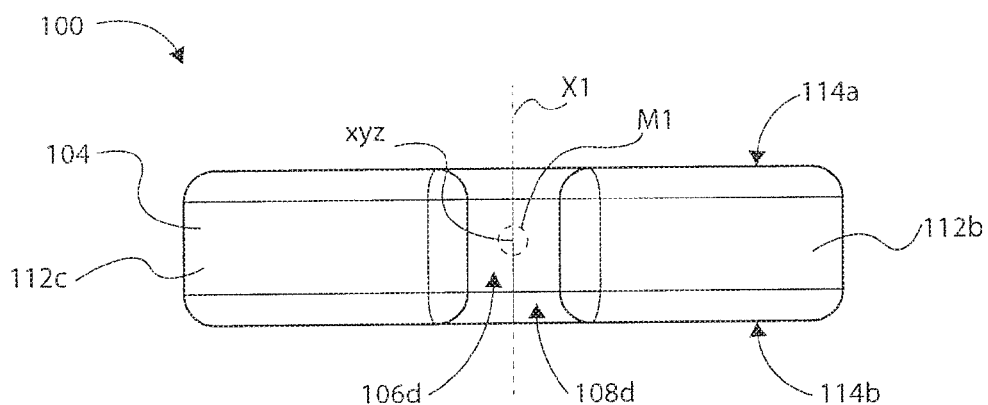
FIG. 1C illustrates a front side view of the multi-IV set retention device of FIG. 1A.
Figure 2:
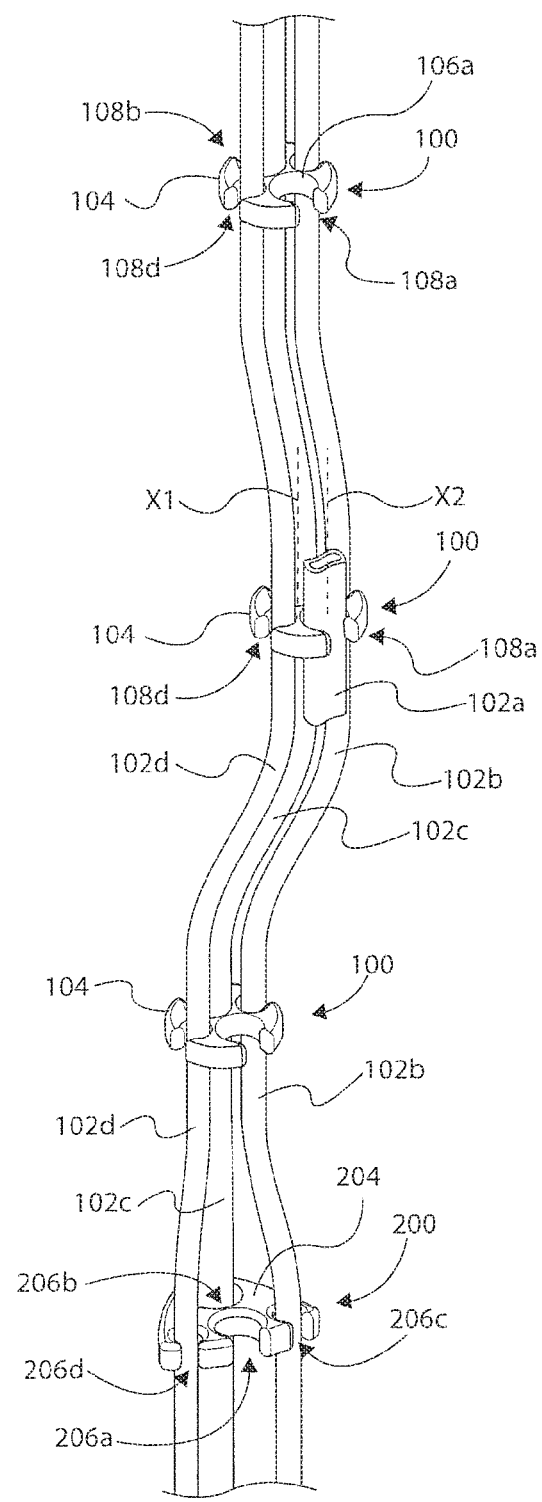
FIG. 2 illustrates a system for retaining and managing a plurality of flexible lines of a plurality of IV sets with a plurality of a set retention devices, in accordance with one exemplary embodiment of the present invention.

FIGS. 1A-2 illustrate a multi-IV set retention device 100 for retaining and managing a plurality of flexible lines 102a-d, as shown in FIG. 2 in one example. The flexible lines 102a-d may be fluid flow lines, such as found in one or more respective IV sets, for instance. It is noted that although the term "multi-line IV set retention device" is used throughout this disclosure, that this is not intended to be limiting in any way. Indeed, it is contemplated that other types of medical lines having a degree of flexibility can be used with the example retention devices described herein. As an overview, the multi-IV set retention device 100 can comprise a retention body 104 having a normal axis X1, and a plurality of retention slots 106a-d formed through the retention body 104. As shown in FIG. 2, each retention slot 106a-d can be sized to removably receive and retain a respective flexible line 102a-d. For instance, each retention slot 106a-d can comprise a generally circular-shaped cross-sectional configuration to retain a respective flexible line also having a generally circular-shaped cross-sectional configuration. The retention slots 106a-d can be sized smaller than, the same size as, or larger than the outer perimeter of the flexible lines 102a-d. In one example, the retention slots 106a-d can be sized slightly smaller than the outer perimeter of flexible lines 102a-d so as to not allow retention devices to move on their own, but require only minimal pressure to move. In one example, the retention slots 106a-d can be sized the same as the outer perimeter of the flexible lines 102a-d so as to facilitate sliding between the flexible lines 102a-d and the multi-IV set retention device 100. A plurality of openings 108a-d each extend from a perimeter area 110 of the retention body 104, and each opening 108a-d is in communication with one of the plurality of retention slots 106a-d. Each opening 108a-d is operable to facilitate insertion and removal of a respective flexible line 102a-d into an associated one of the plurality of retention slots 106a-d for retention of the flexible lines 102a-d. Notably, the retention slots 106a-d are radially arrayed about the normal axis X1 of the retention body 104, which is centrally located at a center-point of the multi-IV set retention device. In this manner, as further detailed below, the plurality of flexible lines 102a-d are somewhat collected or bundled together radially in an array, such that the plurality of flexible lines 102a-d is movable as a unitary body about multiple different axes (i.e., the collection of flexible lines 102a-d can bend or rotate easily about multiple x, y and z axes). In other words, the flexible lines 102a-d can effectively act as a single flexible line because of this radially arrayed arrangement of the retention slots 106a-d retaining the flexible lines 102a-d, as will be further appreciated from the below detailed description. Moreover, in some examples, the retention slots 106a-d can be configured such that the flexible lines 102a-d can slide within the retention slots 106a-d, respectively, to facilitate easier bending about multiple axes of the collection of flexible devices in the formed IV set retention system than would otherwise be possible if the flexible lines were not permitted to slide. Again, a slight interference fit may be needed so that the retention devices do not readily move on their own with respect to each other or retained lines, but still slide in response to movement or bending of the collective grouping of retained IV sets. However, retention slots sized the same as or slightly larger may also accomplish the same function providing less friction between the flexible lines and the retention device(s) 100.

With more specificity, outer surfaces or perimeter surfaces 112a-d of the multi-IV set retention device 100 can have a lateral curved profile (e.g., curvilinear as shown), and can be formed vertically parallel relative to each other and relative to the normal axis X1. Thus, the perimeter surfaces 112a-d can define the perimeter area 110 laterally around the entire multi-IV set retention device. The defined perimeter area 110 can therefore be generally circularly shaped, although other shapes are possible, such as shapes of other examples discussed below. In other words, the perimeter area 110 can define a generally radial perimeter or radial perimeter profile configuration about axis X1. The multi-IV set retention device 100 can further comprise an upper planar surface 114a and an opposing lower planar surface 114b, which can be formed generally orthogonal to the perimeter surfaces 112a-d and to the normal axis X1. In this manner, the multi-IV set retention device 100 can be somewhat formed as a disk having a cylindrical shape, as further shown in FIG. 1C. This is not intended to be limiting, however, as will be apparent from other examples discussed herein, and shown in the drawings. The perimeter surfaces 112a-d can transition to respective upper and lower planar surfaces 114a and 114b by chamfered or radial surfaces (e.g., curved radius or planar chamfers), which will not be labeled for purposes of illustration clarity. Such chamfered or radius surfaces help to reduce the likelihood that the multi-IV set retention device 100 will damage or cut the flexible lines 102a-d.

Alternatively, the perimeter surfaces 112a-d can transition to respective upper and lower planar surfaces 114a and 114b via ninety-degree edge portions. In other examples, the multi-IV set retention device 100 can instead be formed having a spherical shape, hemispherical shape, ovoid shaped, cuboid shape, or other three dimensional shape having similar retention slots as shown in FIG. 1A, or as in other examples discussed herein.

Because the openings 108a-d are also formed radially in an array about the normal axis X1, or rather the center-point of the multi-IV set retention device 100, each opening 108a-d faces outwardly from a central portion 116 of the retention body 104, such that the openings 108a-d face in different directions relative to each other. That is, openings 108a and 108b face outwardly and in opposite directions from each other, while openings 108c and 108d face outwardly and in opposite directions from each other (and face in a direction orthogonal to the adjacent openings 108a and 108b). Said another way, a particular opening that is adjacent other openings are formed to face orthogonally relative to the adjacent openings (e.g., openings 108c and 108d face in directions that are orthogonal to opening 108a). Other opening offsets other than orthogonal are contemplated, as will be apparent from the description herein.

Each opening 108a-d includes opposing gap surfaces that facilitate receiving and retaining and removing respective flexible lines 102a-d. For instance, opening 108a includes opposing gap surfaces 118a and 118b that are formed parallel to each other and to the normal axis X1, and that define a gap distance D1 (FIG. 1B). The gap distance D1 may be slightly smaller than an outer diameter of the flexible line 102a, for instance, so that the flexible line 102a can slightly compress inwardly when a user laterally pushes the flexible line 102a through the opening 108a. IV Sets are typically standard bore and small bore in nature. For example, a standard outside diameter (OD) is typically 0.160-0.140 inches, and a small bore OD is typically 0.090-

0.070 inches. Note that openings of different sizes can be nested together is such a way as to minimize the diameter of any particular multi-IV set retention device exemplified herein.

In some examples, the flexible line can be a polyurethane or PVC material formed as a medical fluid line (i.e., an IV set). The flexible line can comprise any other types of flexible fluid transmitting lines. Therefore, the opposing gap surfaces 118a and 118b are formed in this manner to assist to retain the flexible line 102a within the retention slot 106a, because the flexible line 102a would need to be pulled by a user with sufficient force to re-compress the flexible line 102a in order to squeeze out through the gap surfaces 118a and 118b.

The retention slots 106a-d are each formed inwardly from respective openings 108a-d toward the central portion 116, and each retention slot 106a-d includes a respective line support surface 120a-d. Each line support surface 120a-d can be generally circular or curvilinear in shape about a z-axis, and can have a diameter slightly smaller than (or equal to) an outer diameter of a fluid line received therein. Each line support surface 120a-d can be formed generally vertically parallel relative to the normal axis X1, and can be formed 180 degrees or more in a circular manner as extending from the gap surface 118a around to the opposing gap surface 118b (or even 300 degrees or more). Chamfered or radius surfaces can also be formed about the top, bottom and sides of the line support surfaces 120a-d and to adjoining surfaces of the retention body 104. Thus, the entire retention body 104 can have chamfered or radius surfaces or edge portions being outwardly curved so that the multi-IV set retention device 100 does not have any sharp edges, which reduces the likelihood of the multi-IV set retention device 100 from damaging the flexible lines 102 a-d, and even causing discomfort to personnel using or rubbing against the multi-IV set retention device 100.

As shown in FIG. 1B, the retention slots 106a-d can have a respective central axis A1-A4 that extends generally parallel to the normal axis X1. The central axes A1-A4 are generally situated at a center defined by the circumferential shape of the line support surfaces 120a-d. The central axes A1-A4 are positioned radially around the normal axis X1, such that the central portion 116 is disposed or located between, and surrounded by, the central axes A1-A4. Note that the central portion 116 can be at or near an exact center point of the retention body 104, and can define the x-y-z axes, as illustrated in FIG. 1B.

Thus, in this example, central axis A1 and central axis A2 are laterally situated and radially arrayed to be opposite one another on either side of the normal axis X1 extending through the center-point 116 and generally along the x-axis (the x-axis extending through the center point 116). Furthermore, the central axis A1 and the central axis A2 are substantially equidistance from the normal axis X1 extending through the center-point 116. Similarly, central axis A3 and central axis A4 are situated and radially arrayed to be opposite one another on either side of the normal axis X1 extending through the center-point 116 and generally along the y-axis (the y-axis also extending through the center-point 116). The central axis A3 and the central axis A4 are substantially equidistance from the normal axis X1 extending through the center-point 116, which distance is different (greater in this case) than the distance of central axes A1 and A2 from the normal axis X1 extending through the center-point 116. At least a portion of the retention slots 106a and 106b intersect the x-axis, while at least a portion of the retention slots 106c and 106d intersect the y-axis. These are some explanations of what it means to be "radially arrayed" about the normal axis X1 and the center-point 116, because the axes A1-A4 are radially arrayed or situated around the normal axis X1 because of the shape and position and orientation of the respective retention slots 106a-d relative to the normal axis and to one another, as exemplified above.

It is noted that the axes A1-A4 are situated in a non-linear or non-planar manner relative to each other (or in other words, these are situated about a curved plane parallel to the normal axis), because each retention slot 106a-d is formed in a non-linear manner relative to at least two other retention slots. Adjacent retention slots are formed transverse relative to each other. In other words, retention slots 106b and 106d are formed about respective planes oriented transverse to retention slot 106a, which transverse planes are linear and oriented parallel to and extend from the normal axis.

Figure 4:
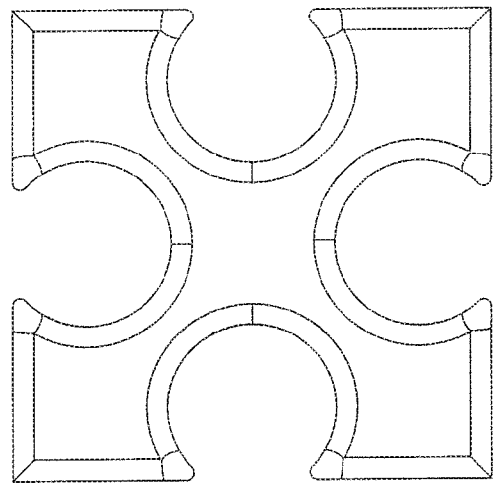
FIG. 4 illustrates top view of a multi-IV set retention device for retaining and managing flexible lines of a plurality of IV sets in accordance with an exemplary embodiment of the present invention.

In this example, the multi-IV set retention device 100 is substantially symmetrical along the x-axis, and also substantially symmetrical along the y-axis. Here, retention slots 106a and 106b are similarly shaped and sized, while retention slots 106c and 106d are similarly shaped and sized (and smaller in diameter or shape than retention slots 106a and 106b). However, all the retention slots 106a-d can be the same size and shape, as shown in FIG. 4. Because of this "symmetry", and because of the "radially arrayed" configuration discussed above, the multi-IV set retention device 100 is generally balanced in mass or weight along both the x-axis and the y-axis. This is notable because the plurality of flexible lines 102a-d can be radially collected or bundled together when each line is coupled to respective retention slots 106a-d, in a manner so that the plurality of flexible lines 102a-d is movable as a unitary body. In other words, the flexible lines 102a-d can effectively act as a single flexible line (i.e., one that can bend or rotate easily in multiple axes as opposed to a collection of flexible lines arrayed linearly (e.g., within a linear plane) relative to one another) because of the radially arrayed arrangement of the retention slots 106a-d. In the example where the flexible lines 102a-d are medical fluid lines, such as IV lines or sets, each line of the same size will be generally the same mass proximate the multi-IV set retention device 100, and each line will be capable of transferring approximately the same mass or weight in fluid. Because of this, a center of mass M1 (FIG. 1C) defined by the mass of the multi-IV set retention device 100 (and the mass of a section of any coupled fluid lines through the retention device 100 (carrying; or not carrying fluid)) will be approximately located substantially at (or exactly at) the central most area or portion of the multi-IV set retention device 100 as shown by the dashed circle labeled MI in FIG. 1C, which is at or near the x-y-z axis of the multi-IV set retention device 100. Of course with other multi-IV set retention devices, the location of the center of mass may be elsewhere than as shown in FIG. 1C, depending upon the configuration of the multi-IV set retention device, as will be appreciated by those skilled in the art.

With continued reference to FIG. 2, each flexible line 102a-d can comprise a longitudinal central axis that extends through a centroid of the circular cross sectional area of the flexible line. Note that only one is labeled as longitudinal central axis X2 extending through a cut-off section of flexible line 102a coupled into retention slot 106a, but it will be appreciated that each flexible line will have a similar longitudinal central axis. When some or all of the flexible lines 102a-d are coupled to a particular multi-IV set retention device 100, the longitudinal central axis of each flexible line 102a-d remain substantially parallel to the longitudinal central axes of other flexible lines when the flexible lines are moved, and at a location proximate the multi-IV set retention device 100 (e.g., a few inches along the flexible lines on either side of the multi-IV set retention device that coupled the lines together). And, such longitudinal central axes remain generally parallel to the normal axis X1 proximate the multi-IV set retention device 100 when the flexible lines 102a-d are moved. This is because of the aforementioned "radially arrayed" configuration that somewhat bundles or collects the flexible lines 102a-d in a radial group in a manner such that the respective masses of the flexible lines 102a-d (and the fluid therein) define a longitudinal center of mass that extends along or very near the normal axis X1 of the multi-IV set retention device 100.

In one example, a plurality of multi-IV set retention devices 100 can be coupled to the flexible lines 102a-d and spaced apart from each other along a length of the flexible lines 102a-d, as illustrated in FIG. 2. In the example where the flexible lines 102a-d are IV fluid lines for medical use, such flexible lines generally have an appreciable, known strain and flexibility. Because of this, the plurality of multi-IV set retention devices 100 can be spaced apart at a minimum distance from each other such that each flexible line is limited from substantial movement away from adjacent, collected flexible lines. For instance, adjacent multi-IV set retention devices can be spaced apart 12 inches (or less) from each other, so that along a length of 4 to 5 feet, the selected number of multi-IV set retention devices collectively generate or define a unitary body of flexible lines that effectively act and move as one flexible line. This is because the flexible lines would be tightly bunched together radially and along such distance of the IV fluid lines, for instance. Thus, if a user grabs and pulls one or more flexible lines from any location, the entire collection of flexible lines will move as one single flexible line that may have a dynamically movable center of mass that extends in a snake-like manner through a central axis or region of the group of flexible lines as they move much like a snake moves). Moreover, if a user pulls a medical device, or moves a patient, coupled to the flexible lines, the unitary body defined by the collection of radially arrayed flexible lines would also move in a similar snake like manner, so that any one particular line is not dangling or straggling behind other lines, which could cause it to become entangled with other structures or personnel. This is a common problem with prior retention clips or devices that couple fluid lines only in a linear manner along a plane, which makes the collection of lines unwieldy to move around a hospital room and around a patient, for instance, as discussed above. However, with the present technology discussed herein, because the flexible lines 102a-d are grouped or collected in a radial array as discussed above, the flexible lines and the multi-IV set retention devices avoid such aforementioned problems when being moved or managed.

The IV set retention system shown in FIG. 2 can comprise an IV set system, which can further include a gravity-based IV solution bag fluidly coupled to the flexible lines 102a-d at an upper area via access ports, while distal end(s) of the flexible lines 102a-d can be fluidly coupled to a patient. Multiple line systems are generally brought together in the primary IV set, which is then connected to one patient access point. A number of access points and access ports can be included and located on the flexible lines for delivering medication to the patient, and a number of manifolds could be coupled to the fluid lines. Having an IV set system retained and managed by one or more multi-IV set retention devices provides an additional advantage of being able to locate access points or ports anywhere along the length of the one or more IV sets secured and retained within the one or more multi-IV set retention devices. Placement of access points and access ports anywhere along the length of the one or more IV sets is not possible with prior co-extruded multiple IV set systems. Furthermore, in some examples, the arrayed arrangement of the IV sets as retained within the one or more multi-IV set retention devices, as discussed herein, allows access ports to be located anywhere around the 360 degree circumference of the arrayed IV set retention system. An additional advantage is that the IV set retention system can be assembled (i.e., one or more IV sets retained within one or more multi-IV set retention devices) and disassembled (i.e., one or more IV sets removed from the one or more multi-IV set retention devices) and then reassembled in whole or in part as needed or desired. Or, the IV set retention system can comprise IV sets that were previously joined together and then stripped away, such that these lines are essentially rejoined to one another (albeit via the one or more multi-IV set retention systems). Such is beneficial, for example, in an Intensive Care Unit (ICU) setting where any or all of the anesthesia lines previously separated from one another in some cases stripped away from one another if previously physically joined together), or removed from an already assembled IV set retention system, or other non-anesthesia ICU care lines can be brought back together, or included, and bundled together by causing them to be retained within one or more multi-IV set retention devices, thus forming a new IV set retention system or reassembling one previously in existence. Although these advantages are discussed in relation to the example shown in FIGS. 1-2, these are applicable to the other example multi-IV set retention systems discussed herein. It is possible with very complex cases more than four or five, or in the case of FIG. 6 six, IV sets may be needed. Another advantage that the retention devices disclosed herein provide is that IV sets from two different bundles or IV set retention systems can be joined together, thus thrilling a multi-bundle arrayed system. For example, an IV set from a first bundled array in a first IV set retention system can be common to a second bundled array in a second IV set retention system.

Figure 3A:
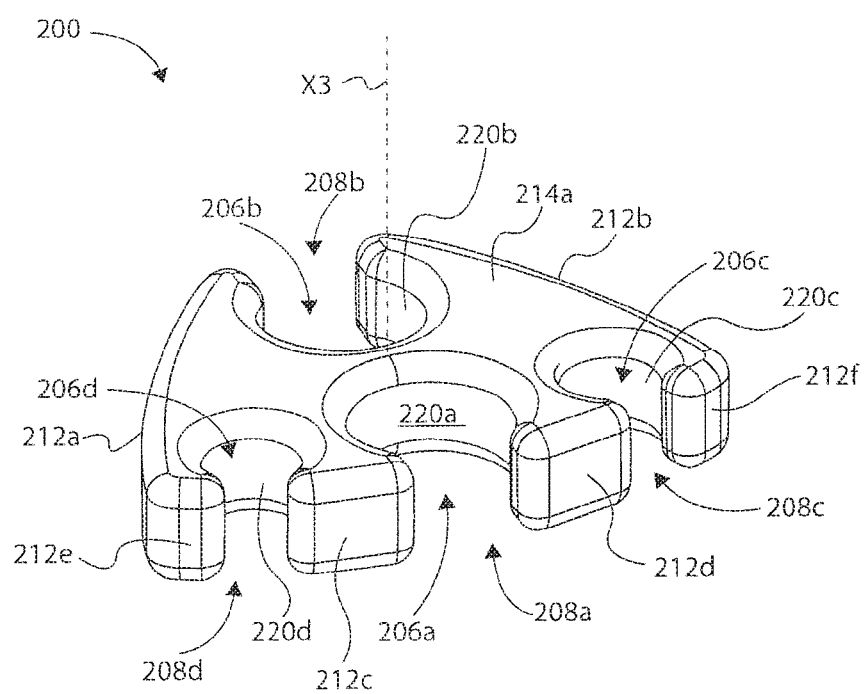
FIG. 3A illustrates an isometric view of a multi-IV set retention device for retaining and managing flexible lines of a plurality of IV sets in accordance with an exemplary embodiment of the present invention.
Figure 3B:
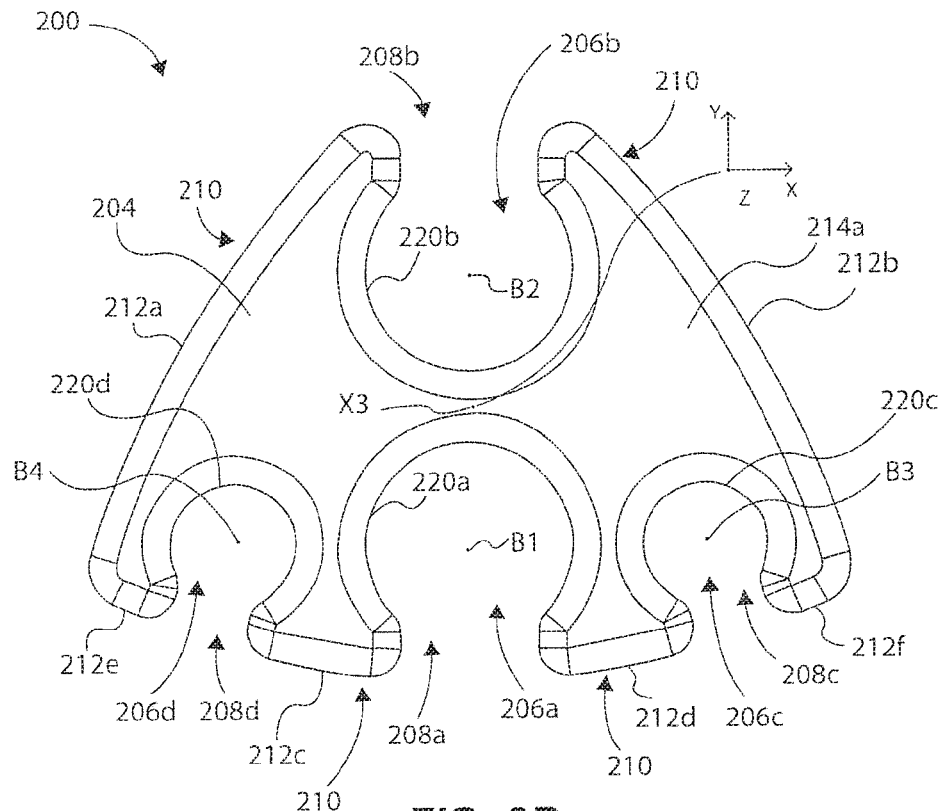
FIG. 3B illustrates a top view of the multi-IV set retention device of FIG. 1A.
Figure 3C:
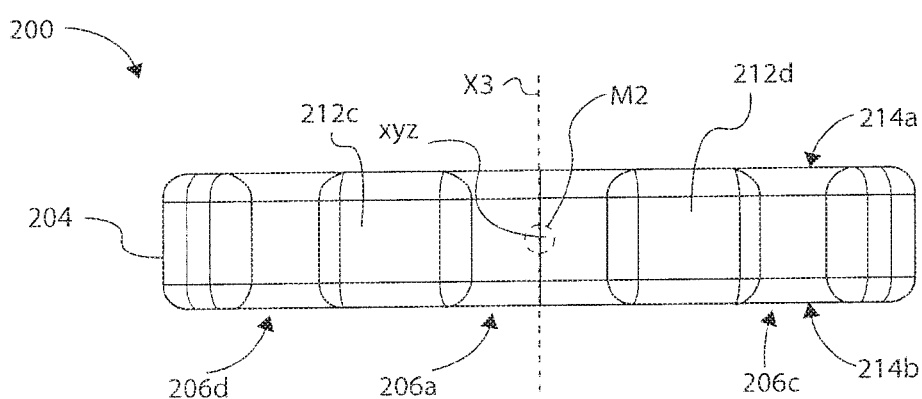
FIG. 3C illustrates a front side view of the multi-IV set retention device of FIG. 1A.

FIGS. 3A-3C illustrate a multi-IV set multi-IV set retention device 200 for retaining and managing flexible lines 102a-d, such as those of a plurality of respective IV sets, as shown in the lower section of the flexibles line shown in FIG. 2. Note that multi-IV set retention device 200 can be similarly shaped and formed as multi-IV set retention device 100 in some aspects, but also different in other aspects, as detailed below. Therefore, the similar aspects will not be discussed in as great detail, but it should be readily appreciated that such similarities will have similar advantages.

As an overview, the multi-IV set retention device 200 can comprise a retention body 204 defining a normal axis X3, and a plurality of retention slots 206a-d formed through the retention body 204. As shown in FIG. 2, each retention slot 206a-d can be sized to removably receive and retain a respective flexible line 102a-d, and each retention slot 206a-d can comprise a generally circular-shaped configuration. A plurality of openings 208a-d each extend from a perimeter area 210 of the retention body 204, and each opening 208a-d is in communication with one of the plurality of retention slots 206a-d. Each opening 208a-d is operable to facilitate insertion of a respective flexible line 102a-d into an associated one of the plurality of retention slots 206a-d for retention of the respective flexible line 102a-d. Notably, the retention slots 206a-d are radially arrayed about the normal axis X3 of the retention body 204. In this manner, as further detailed below (and similarly discussed above regarding multi-IV set retention device 100), the plurality of flexible lines 102*a-d* are somewhat collected or bundled together radially, such that the plurality of flexible lines 102*a-d* is movable as a unitary body. In other words, the flexible lines 102*a-d* can effectively act as a single flexible line because of the arrayed radial arrangement of the retention slots 206*a-d* coupling together in a radial manner the plurality of flexible lines 102*a-d.*

With more specificity, outer surfaces or perimeter surfaces 212*a-f* of the multi-IV set retention device 200 can each have a curved profile, and can be formed generally parallel relative to each other and relative to the normal axis X3, so that the perimeter surfaces 212*a-f* define the perimeter area 210. The perimeter area 210 can therefore be generally triangularly shaped or pennant shaped in a three-dimensional disk shape (FIG. 3C), The multi-IV set retention device 200 can further comprise an upper planar surface 214*a* and an opposing lower planar surface 214*b*, which can be formed generally orthogonal to the perimeter surfaces 212*a-d* and to the normal axis X3. The perimeter surfaces 212*a-f* can transition to respective upper and lower planar surfaces 214*a* and 214*b* by chamfered surfaces, similar as described regarding multi-IV set retention device 100.

Because the openings 208*a-d* are formed and arranged radially in an array, each opening 208*a-d* faces outwardly from a center portion 216 of the retention body 200, such that the openings 208*a-d* face different directions relative to each other. That is, openings 208*a* and 208*h* face outwardly and in opposite directions from each other, while openings 208*c* and 208*d* face outwardly and about linear planes oriented in transverse directions relative to each other, which planes extend radially outward from the normal axis, or extend through the normal axis. In this example, at least some of the retention slots 206*a-d* are radially arrayed in an arc about the retention body 204. This is best shown in FIG. 3B, showing retention slots 206*a*, 206*c,* and/or 206*d* being arranged in an arc-like manner relative to each other, This better exposes the retention slots 206*a-d* to receive flexible lines so they do not get bunched up, and so that the flexible lines retained therein are closer to the central portion 216 (as opposed to linearly situated retention slots), which helps to place the center of mass near or at the central portion 216, for similar advantages discussed regarding multi-IV set retention device 100, Each opening 208*a-d* includes opposing gap surfaces that facilitate receiving and retaining respective flexible lines, in a similar manner as described regarding multi-IV set retention device 100.

The retention slots 206*a-d* are each formed inwardly from respective openings 208*a-d* toward the central portion 216, and each opening 208*a-d* includes a respective line support surface 220*a-d*. Note that the central portion 216 may not be at an exact center of the device 200; rather, it can be the area or portion disposed between retention slots 206*a* and 206*b*. Each line support surface 220*a-d* can be generally circular or curvilinear in shape, and can have a diameter slightly smaller than (or equal to) an outer diameter of a fluid line received therein. Each radial line support surface 220*a-d* can be formed generally vertically and parallel relative to the normal axis X3, and can be formed to be 180 degrees or more in a circular manner as extending between gap surfaces (or even 300 degrees or more). Chamfered or radius surfaces can also be formed about the top, bottom and sides of the radial line support surfaces 220*a-d*, and to adjoining surfaces of the retention body 200. Thus, the entire retention body 200 can have chamfered or radius surfaces or edge portions being outwardly curved so that the multi-IV set retention device 200 does not have any sharp edges or ninety-degree corner portions.

As shown in FIG. 3B, the retention slots 206*a-d* can have a respective central axis B1-B4 that are each generally parallel to the normal axis X3. The central axes B1-B4 are generally situated at a center or centroid defined by the circumferential shape of the line support surfaces 220*a-d*. The central axes B1-B4 can be positioned radially around the normal axis X3, such that the central portion 216 is disposed or located between, and surrounded by, at least some of the central axes B1-B4. Thus, central axis B1 and central axis B2 are situated on either side of the normal axis X3 and generally along the y-axis, and are substantially equidistance from the normal axis X3 extending through the center-point of the multi-IV set retention device 200. And, central axis B3 and central axis B4 are situated on either side of the normal axis X3 and generally along a plane that is parallel to the x-axis, and are substantially equidistance from the normal axis X3. Said another way, at least a portion of the retention slots 206*a* and 206*b* intersect the y-axis, while the retention slots 206*c* and 206*d* are separated from each other along the x-axis. These are some explanations of what it means to be "radially arrayed" about the normal axis X3, because the axes B1-B4 are radially situated around the normal axis X3 due to the shape and position of the respective retention slots 206*a-d*. Said another way, axes B1-B4 are situated in a non-linear manner relative to each other, because each retention slot 206*a-d* is formed in a non-linear manner relative to at least two other retention slots. Adjacent retention slots are formed transverse relative to each other (e.g., retention slots 206*c* and 206*d* are formed about respective planes oriented transverse to retention slot 206*b,* which transverse planes are linear and oriented parallel to and extend from or through the normal axis).

The multi-IV set retention device 200 is substantially symmetrical along the y-axis. In the example shown, retention slots 206*a* and 206*b* are similarly shaped and sized, while retention slots 206*c* and 206*d* are similarly shaped and sized (and smaller in diameter or shape that retention slots 206*a* and 206*b*). However, all the retention slots 206*a-d* can be the same size and shape, Because of this "symmetry" and because of the "radially arrayed" configuration discussed above, the multi-IV set retention device 200 is somewhat balanced in mass along both the y-axis. This is notable because the plurality of flexible lines 102*a-d* can be radially collected or bundled together when the flexible lines are coupled to respective retention slots 206*a-d*, such that the plurality of flexible lines 102*a-d* is movable as a unitary body. In other words, the flexible lines 102*a-d* can effectively act as a single flexible line because of the radially arrayed arrangement of the retention slots 206*a-d*. In the example where the flexible lines 102*a-d* are medical fluid lines, such as IV lines, each line of the same size will be generally the same mass and will transfer approximately the same mass or weight in fluid. Because of this, a center of mass M2 (FIG. 3C) defined by the mass of the multi-IV set retention device 200 and the mass of a section of the fluid lines (carrying fluid) will be approximately placed substantially at (or exactly at) the central most area or portion of the multi-IV set retention device 200 (i.e., inside the multi-IV set retention device), as shown by the dashed circle labeled M2 in FIG. 3C.

Similarly as described above with reference to FIG. 2, when some or all of the flexible lines 102*a-d* are coupled to the multi-IV set retention device 200, the longitudinal central axis of each flexible line 102*a-d* will remain substantially parallel to the longitudinal central axes of other flexible lines proximate the multi-IV set retention device 200 when the flexible lines are moved. And, such longitudinal central axes remain generally parallel to the normal axis X3 when the lines are moved. This is because of the aforementioned "radially arrayed" configuration that somewhat bundles or collects the flexible lines 102a-d in a radial group around the normal axis, so that their respective masses define a longitudinal center of mass that extends along or very near the normal axis X3 of the multi-IV set retention device 200.

In one example, a plurality of multi-IV set retention devices 200 can be coupled to the flexible lines 102a-d and spaced apart from each other along a length of the flexible lines 102a-d, similarly as described above regarding the plurality of multi-IV set retention devices 100 shown in FIG. 2. Because of this, a plurality of multi-IV set retention devices (i.e., 200s) can be spaced apart at a minimum distance from each other, such that each flexible line is limited from substantial movement away from adjacent flexible lines proximate the multi-IV set retention device. Thus, a plurality of spaced apart multi-IV set retention devices (i.e., 200s) collectively generate a unitary body of lines that effectively act and move as one line, because the flexible lines would be tightly bunched together along such distance of the IV fluid lines, for instance.

Thus, if a user grabs and pulls one particular line, the entire group of flexible lines move as one single flexible line having a dynamically movable center of mass that extends in a snake-like manner through a central axis or region of the group of flexible lines as they move (much like a snake moves). Moreover, if a use pulls a medical device, or moves a patient, coupled to the flexible lines, the unitary body defined by the collection of radially disposed flexible lines would also move in a similar snake-like manner, so that any one particular line is not dangling or straggling behind other lines, which can cause it to "catch" on other structures or personnel. Note that one or more flexible lines can be removed, left in place, or replaced by new lines after such one or more (old) flexible lines have been removed. This is advantageous in cases where anesthesia drug lines need removed from a particular IV set system prior to departure of the patient from a recovery area at a medical facility. In this way, adding lines back into the IV set system about the multi-IV set retention device(s) can be beneficial, such as if the patient is moved from one area to another area (e.g., ICU where multiple line IV set systems are routinely used).

Figure 5:
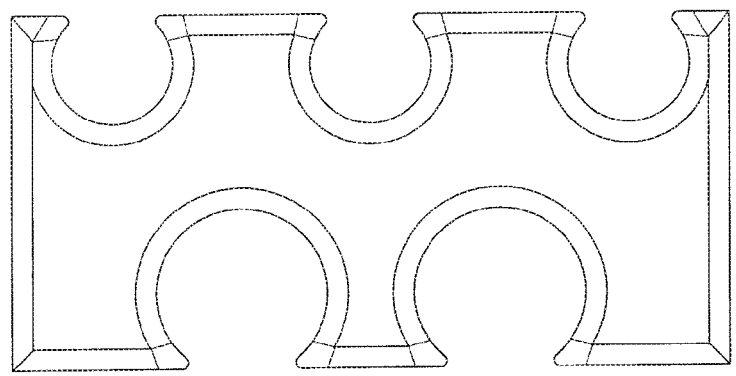
FIG. 5 illustrates top view of a multi-IV set retention device for retaining and managing flexible lines of a plurality of IV sets in accordance with an exemplary embodiment of the present invention.
Figure 6:
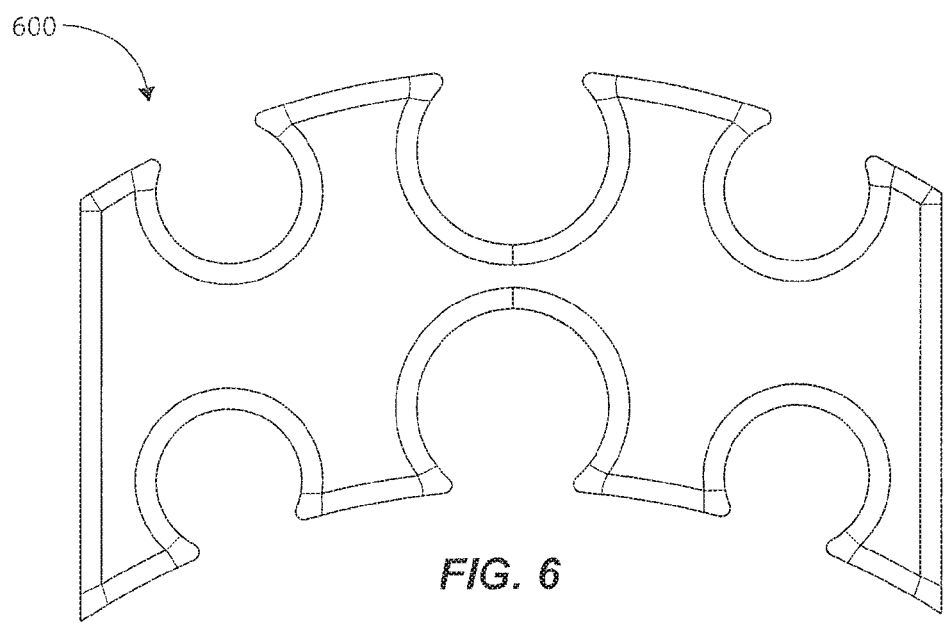
FIG. 6 illustrates top view of a multi-IV set retention device for retaining and managing flexible lines of a plurality of IV sets in accordance with an exemplary embodiment of the present invention.
Figure 7:
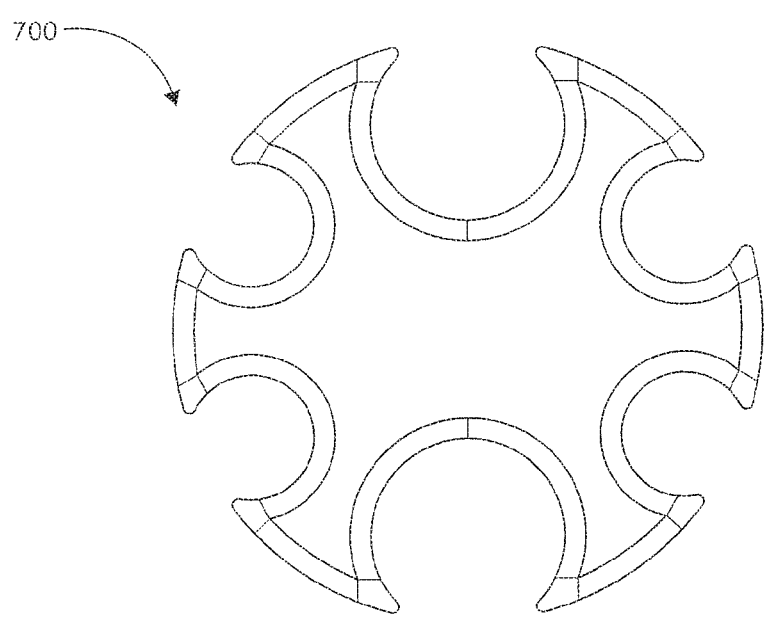
FIG. 7 illustrates top view of a multi-IV set retention device for retaining and managing flexible lines of a plurality of IV sets in accordance with an exemplary embodiment of the present invention.

FIGS. 4-7 illustrates a variety of differently shaped multi-IV set retention devices that each have a retention body having a plurality of retention slots being radially arrayed about a normal axis of the retention body. For example, FIG. 4 shows a multi-IV set retention device 400 having a square disk shape and a plurality of openings formed similarly to multi-IV set retention device 100 described above; however, the openings of the multi-IV set retention device 400 are all the same size and shape. FIG. 5 shows a multi-IV set retention device 500 having a rectangular disk shape and a plurality of openings formed along opposing longitudinal sides of the multi-IV set retention device 500. FIG. 6 shows a multi-IV set retention device 600 having an arced rectangular disk shape and a plurality of openings formed along opposing longitudinal/radial sides of the multi-IV set retention device 600. Finally, FIG. 7 shows a multi-IV set retention device 700 having a circular disk shape and a plurality of openings formed radially around a perimeter area of the multi-IV set retention device 700, similar to multi-IV set retention device 100 shown in FIG. 1A, but having six retentions slots instead of four.

It should be appreciated that the multi-IV set retention devices of FIGS. 4-7 can have the same or similar features as described regarding multi-IV set retention devices 100 and 200 discussed above, such as a normal axis extending through a central portion or area of the device, and retention slots arrayed radially about the normal axis. Therefore, such examples of FIGS. 4-7 can have the same advantages of retaining and managing fluid lines in a radial collection or bundle around a normal axis so that the fluid lines can move essentially as a unitary body, and/or act as a single flexible line.

The multi-IV set retention devices contemplated herein can be a rigid or semi-rigid construction, such as a unitary body formed of a plastic, polymer, composite, or other such suitable material. The multi-IV set retention devices contemplated herein can be formed by machining, molding, fusion, printing, injection, or other suitable forms of manufacturing a rigid or semi-rigid body comprised of such suitable materials.

It is to be understood that the embodiments of the invention disclosed are not limited to the particular structures, process steps, or materials disclosed herein, but are extended to equivalents thereof as would be recognized by those ordinarily skilled in the relevant arts. It should also be understood that terminology employed herein is used for the purpose of describing particular embodiments only and is not intended to be limiting.

Reference throughout this specification to "one embodiment" or "an embodiment" means that a particular feature, structure, or characteristic described in connection with the embodiment is included in at least one embodiment of the present invention. Thus, appearances of the phrases "in one embodiment" or "in an embodiment" in various places throughout this specification are not necessarily all referring to the same embodiment.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary. In addition, various embodiments and example of the present invention may be referred to herein along with alternatives for the various components thereof. It is understood that such embodiments, examples, and alternatives are not to be construed as de facto equivalents of one another, but are to be considered as separate and autonomous representations of the present invention.

Furthermore, the described features, structures, or characteristics may be combined in any suitable mariner in one or more embodiments. In the description, numerous specific details are provided, such as examples of lengths, widths, shapes, etc., to provide a thorough understanding of embodiments of the invention. One skilled in the relevant art will recognize, however, that the invention can be practiced without one or more of the specific details, or with other methods, components, materials, etc. In other instances, well-known structures, materials, or operations are not shown or described in detail to avoid obscuring aspects of the invention.

While the foregoing examples are illustrative of the principles of the present invention in one or more particular applications, it will be apparent to those of ordinary skill in the art that numerous modifications in form, usage and details of implementation can be made without the exercise of inventive faculty, and without departing from the principles and concepts of the invention.

The invention claimed is:

1. A multi-IV set retention system, comprising:
a plurality of IV sets, each comprising a flexible fluid line;
a multi-IV set retention device operable to retain the plurality of IV sets, the multi-IV set retention device comprising:
a rigid retention body having a normal axis, and a perimeter area comprising multiple perimeter sides, each perimeter side having a curved surface along its length;
a plurality of retention slots formed through the rigid retention body, each retention slot sized to removably receive and retain the flexible fluid line of one of the plurality of IV sets; and
a plurality of nondeforming openings extending from one of the perimeter sides of the rigid retention body, each nondeforming opening being in communication with one of the plurality of retention slots,
wherein at least two of the plurality of retention slots and associated two of the plurality of openings being formed along a common perimeter side of the plurality of perimeter sides,
wherein each respective nondeforming opening comprises opposing gap surfaces having a gap distance smaller than a diameter of a flexible fluid line of a respective one of the plurality of IV sets, such that each nondeforming opening is operable to compress the respective flexible fluid line of the respective IV set inserted there through into an associated one of the plurality of retention slots,
wherein the plurality of retention slots are radially arrayed about the normal axis of the rigid retention body.

2. The multi-IV set retention device of claim 1, wherein each nondeforming opening faces outwardly from a central portion of the rigid retention body, and wherein the nondeforming openings outwardly face different directions relative to each other.

3. The multi-IV set retention device of claim 1, wherein the plurality of retention slots are formed and arrayed in a non-linear manner about the rigid retention body, these being oriented about a curved plane.

4. The multi-IV set retention device of claim 1, wherein at least some of the retention slots are arrayed in an arc about the rigid retention body.

5. The multi-IV set retention device of claim 1, wherein adjacent retention slots are formed and oriented about respective planes transverse to each other and parallel to and extending through the normal axis.

6. The multi-IV set retention device of claim 1, wherein the normal axis is centrally located about the rigid retention body relative to a central axis of each of at least two of the retention slots.

7. The multi-IV set retention device of claim 1, wherein a first retention slot comprises a first central axis situated generally along an x-axis of the rigid retention body, and wherein a second retention slot comprises a second central axis situated generally along a y-axis of the rigid retention body.

8. The multi-IV set retention device of claim 1, wherein a first pair of retention slots is situated generally along an x-axis of the rigid retention body, and wherein a second pair retention slots is situation generally along a y-axis of the rigid retention body.

9. The multi-IV set retention device of claim 1, wherein each retention slot comprises a radial line support surface substantially parallel to the normal axis and formed radially in at least 180 degrees.

10. The multi-IV set retention device of claim 1, wherein each of the plurality of retention slots comprises opposing wall portions separated by a distance that measures less than a diameter of a flexible fluid line of a respective IV set, such that each of the plurality of retention slots applies a compression force to the flexible fluid line of the respective IV set retained therein, thereby reducing the diameter of a portion of the flexible fluid line.

11. The multi-IV set retention device of claim 1, wherein central axes of at least two retention slots are substantially equidistance from a center-point of the multi-IV set retention device.

12. The multi-IV set retention device of claim 1, wherein the rigid retention body is substantially symmetrical along an x-axis and along a y-axis, such that, when a flexible fluid line is retained in each of the retention slots, the multi-IV set retention device and the flexible fluid lines move as a unitary body having a longitudinal center of mass extending generally through a central portion of the rigid retention body.

13. The multi-IV set retention device of claim 1, wherein each retention slot comprises a central axis being substantially parallel to the normal axis, and wherein the normal axis is centrally located relative to the central axes of at least two retention slots.

14. An IV set retention system for retaining a plurality of IV sets, comprising:
a plurality of flexible fluid lines of a plurality of respective IV sets; and
a plurality of multi-IV set retention devices removably coupled to the plurality of flexible fluid lines, each multi-IV set retention device comprising a rigid retention body having a perimeter area comprising multiple perimeter sides, each perimeter side having a curved surface along its length, and a plurality of retention slots formed through and radially arrayed about the rigid retention body, each retention slot having a nondeforming opening sized to removably receive and compress one of the flexible fluid lines of the plurality of flexible fluid lines, wherein each retention slot is sized to retain the respective received flexible fluid line,
wherein at least two of the plurality of retention slots and associated two of the plurality of openings are formed along a common perimeter side of the plurality of perimeter sides, and
wherein the multi-IV set retention devices are spaced apart from each other along a length of the plurality of flexible fluid lines, such that the plurality of flexible fluid lines is movable as a unitary body.

15. The IV set retention system of claim 14, wherein each flexible fluid line comprises a longitudinal central axis that remains substantially parallel to the longitudinal central axes of other flexible fluid lines when the flexible fluid lines are moved along with the plurality of multi-IV set retention devices.

16. The IV set retention system of claim 14, wherein the unitary body defined by the plurality of flexible fluid lines defines a center of mass defined about a central portion of each rigid retention body.

17. The IV set retention system of claim 14, wherein the retention bodies are spaced apart at a minimum distance from each other, such that the flexible fluid lines are bundled in a radial array such that each line is limited from substantial movement away from adjacent flexible fluid lines.

18. The IV set retention system of claim 14, wherein the plurality of flexible fluid lines comprises a plurality of fluid lines capable of transferring a medical fluid through the fluid lines to a patient, wherein respective segments of the plurality of flexible fluid lines, upon having the medical fluid therein, through the multi-IV retention system defines a center of mass defined about a central portion of each rigid retention body of respective multi-IV set retention devices, such that the plurality of fluid lines move and act as a single flexible fluid line having a generally radial perimeter profile defined by perimeters of the fluid lines.

19. A method of manufacturing a multi-IV set retention device for retaining and managing flexible fluid lines of respective IV sets, comprising:
    forming a rigid retention body having a perimeter area comprising multiple perimeter sides, each perimeter side having a curved surface along its length;
    forming a plurality of retention slots through the rigid retention body; and
    forming a plurality of nondeforming openings that extend from one of the perimeter sides of the rigid retention body, each nondeforming opening formed in communication with one of the plurality of retention slots, and at least two of the plurality of retention slots and associated two of the plurality of openings being formed along a common perimeter side of the plurality of perimeter sides
    wherein each respective nondeforming opening comprises opposing gap surfaces having a gap distance smaller than a diameter of a flexible fluid line of a respective IV set, such that each nondeforming opening is operable to compress a flexible fluid line of a respective IV set and to facilitate insertion of the flexible fluid line of the respective IV set into an associated one of the plurality of retention slots,
    wherein forming the retention slots and nondeforming openings comprises forming the plurality of retention slots to be radially arrayed about the rigid retention body.

20. The method of claim 19, wherein forming the plurality of nondeforming openings comprises forming each nondeforming opening to face outwardly from a central portion of the rigid retention body and to face outwardly in different directions relative to other nondeforming openings.

21. The method of claim 19, wherein forming the plurality of retention slots comprises forming the plurality of retention slots to be arrayed in a non-linear manner, such that adjacent retention slots are formed about planes oriented transverse relative to each other, which transverse planes are linear and oriented parallel to and extend from the normal axis.

22. A method for retaining and managing flexible fluid lines of respective IV sets with at least one multi-IV set retention device, comprising:
    providing a multi-IV set retention device comprising a rigid retention body having a perimeter area comprising multiple perimeter sides, each perimeter side having a curved surface along its length, and a plurality of retention slots radially arrayed about and formed through the rigid retention body, each retention slot having a nondeforming opening, at least two of the plurality of retention slots and associated two of the plurality of openings being formed along a common perimeter side of the plurality of perimeter sides; and
    coupling a flexible line of a plurality of flexible fluid lines into respective retention slots of the plurality of retention slots through the respective nondeforming openings, wherein the flexible fluid lines are caused to be compressed upon being inserted into the respective nondeforming openings, wherein upon being retained in the respective retention slots, the plurality of flexible fluid lines are movable as a unitary body.

23. The method of claim 22, further comprising coupling a plurality of retention devices to the plurality of flexible fluid lines.

24. The method of claim 23, further comprising moving the plurality of flexible fluid lines and the plurality of multi-IV set retention devices, such that a longitudinal central axis of each flexible fluid line remains substantially parallel to the longitudinal central axes of other flexible fluid lines when the flexible fluid lines are moved.

25. The IV set retention system of claim 14, wherein each of the plurality flexible fluid lines are slidably retained in a respective retention slot of a multi-IV set retention device of the plurality of multi-IV set retention devices.

26. The IV set retention system of claim 14, wherein each of the plurality of retention slots of the multi-IV set retention devices comprises opposing wall portions separated by a distance that measures less than a diameter of a flexible fluid line of a respective IV set, such that each of the plurality of retention slots applies a compression force to the flexible fluid line of the respective IV set retained therein, thereby reducing the diameter of a portion of the flexible fluid line.

* * * * *